(12) United States Patent
Dharmadikari et al.

(10) Patent No.: US 10,413,543 B2
(45) Date of Patent: Sep. 17, 2019

(54) STABLE MULTIPARTICULATE PHARMACEUTICAL COMPOSITION OF ROSUVASTATIN

(71) Applicant: SUN PHARMA ADVANCED RESEARCH COMPANY LTD., Mumbai, Maharashtra (IN)

(72) Inventors: Nitin Bhalachandra Dharmadikari, Mumbai (IN); Yashoraj Zala, Mumbai (IN); Ashwini Gadkari, Mumbai (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

(21) Appl. No.: 15/042,479

(22) Filed: Feb. 12, 2016

(65) Prior Publication Data

US 2017/0056401 A1    Mar. 2, 2017

(30) Foreign Application Priority Data

Sep. 1, 2015  (IN) .......................... 3351/MUM/2015

(51) Int. Cl.
| | | |
|---|---|---|
| *A61K 31/505* | (2006.01) | |
| *A61K 9/16* | (2006.01) | |
| *A61K 9/50* | (2006.01) | |
| *A61K 9/48* | (2006.01) | |

(52) U.S. Cl.
CPC .......... *A61K 31/505* (2013.01); *A61K 9/1611* (2013.01); *A61K 9/1617* (2013.01); *A61K 9/1623* (2013.01); *A61K 9/1635* (2013.01); *A61K 9/1652* (2013.01); *A61K 9/4858* (2013.01); *A61K 9/4866* (2013.01); *A61K 9/5031* (2013.01); *A61K 9/5042* (2013.01); *A61K 9/5047* (2013.01)

(58) Field of Classification Search
None
See application file for complete search history.

(56) References Cited

U.S. PATENT DOCUMENTS

| | | | |
|---|---|---|---|
| 5,225,020 A | 7/1993 | Millett et al. | |
| 7,030,151 B2 * | 4/2006 | Kerč | A61K 9/1611 514/422 |
| 7,459,447 B2 * | 12/2008 | Aoki | A61K 31/397 514/210.02 |
| 8,632,807 B2 | 1/2014 | Creekmore et al. | |
| 2004/0180087 A1 * | 9/2004 | Li | A61K 31/22 424/471 |
| 2007/0202159 A1 | 8/2007 | Mathur et al. | |
| 2008/0249120 A1 | 10/2008 | Soni et al. | |
| 2010/0151034 A1 * | 6/2010 | Yano | A61K 9/5015 424/495 |
| 2014/0044784 A1 | 2/2014 | Kim et al. | |

FOREIGN PATENT DOCUMENTS

| | | |
|---|---|---|
| IN | 1230/DEL/2009 A | 12/2010 |
| KR | 10-2009-0091077 A | 8/2009 |
| WO | 2006/006021 A2 | 1/2006 |
| WO | 2008/044236 A2 | 4/2008 |
| WO | 2008/062476 A2 | 5/2008 |
| WO | 2009/156173 A1 | 12/2009 |
| WO | 2012/064307 A1 | 5/2012 |
| WO | 2012/160352 A1 | 11/2012 |
| WO | 2014/140867 A2 | 9/2014 |

\* cited by examiner

*Primary Examiner* — Tigabu Kassa
(74) *Attorney, Agent, or Firm* — Sughrue Mion, PLLC

(57) ABSTRACT

A stable multi-particulate pharmaceutical composition comprising pellets, the pellets comprising a mixture of rosuvastatin or its pharmaceutically acceptable salts as a sole active ingredient, one or more osmotic release modifiers and one or more stabilizers.

5 Claims, No Drawings

STABLE MULTIPARTICULATE PHARMACEUTICAL COMPOSITION OF ROSUVASTATIN

FIELD OF INVENTION

The present invention relates to a stable, multi-particulate pharmaceutical composition of rosuvastatin or its pharmaceutically acceptable salt.

BACKGROUND

Rosuvastatin is marketed as rosuvastatin calcium in the form of tablets containing 5, 10, 20 and 40 mg of rosuvastatin calcium, under the brand name of Crestor®. It is indicated in patients with primary hyperlipidemia as an adjunct to diet to reduce elevated total cholesterol, low density lipoprotein and triglyceride levels and to increase high density lipoprotein. As The prevalence of hyperlipidemia increases with age and requires chronic therapy, these HMG-CoA inhibitors, such as rosuvastatin calcium, are generally prescribed to patients for the rest of their lives. Further, it is known that geriatric populations generally may need to take more than one medication.

Solid unit oral dosage forms are available in a variety of sizes and shapes. It is always preferable to design a dosage form that is patient compliant in terms of adhering to the therapy. Sometimes such solid dosage forms pose problems while swallowing as a result of, example, their size, stickiness, taste, aftertaste or frequency of administration. Particularly, in patients suffering from dysphagia, the swallowing of solid oral dosage form may be very painful, if not impossible. Thus, there is a need for a dosage form that eases oral administration.

SUMMARY OF THE INVENTION

The present inventors have discovered a novel multi-particulate pharmaceutical composition, each particle having a higher percentage of rosuvastain or its pharmaceutically acceptable salt, loaded into it. The high percentage loading makes the single unit dosage form of the pharmaceutical composition compact, and causes it to contain fewer excipients, allowing the patient to administer it by sprinkling onto a minimum portion, for instance, a teaspoon, of a vehicle. The multiparticulate composition has been found to be not only patient compliant but also chemically stable throughout the shelf life of the product.

The present invention provides a stable multi-particulate pharmaceutical composition comprising pellets, the pellets comprising a mixture of rosuvastatin or its pharmaceutically acceptable salts as a sole active ingredient, one or more osmotic release modifiers and one or more stabilizers. Also, the present inventors have discovered a novel stable multi-particulate pharmaceutical composition comprising pellets, the pellets comprising at least 5% by weight of pharmaceutically acceptable salt of rosuvastatin as a sole active ingredient, by weight of the pellets.

The present inventors have discovered that the osmotic release modifiers are critical to accelerate release of rosuvastatin from the pellets. Such a stable multi-particulate pharmaceutical composition of rosuvastatin calcium is particularly advantageous as it can be administered by sprinkling on soft food, such as applesauce, pudding, custard, oatmeal or yoghurt. The pellets are of such a size that they escape chewing or mastication and are palatable. Thus a stable, multi-particulate pharmaceutical composition of rosuvastatin calcium that is very patient compliant is presented. Alternatively, the pellets can also be administered via a nasogastric tubing for hospitalized patients.

DETAILED DESCRIPTION OF THE INVENTION

The term 'pellet' as used herein means any particle that is prepared by process of agglomeration of, for example, powder. The agglomeration may be achieved by either granulation, compaction, extrusion, slugging, drug loading or the like. Such a pellet preferably has good flow, and preferably has an aspect ratio of about 1 to about 2. Further, the pellets may be spherical or oval with a smooth surface and may have a density higher than the powder.

The term "mixture" as used herein means that the rosuvastatin or the pharmaceutically acceptable salts thereof are mixed uniformly with excipients of various categories such as stabilizers, alkalizing agents, buffering agents, disintegrant or diluents etc.

The term 'stable' as used herein means that when the multi-particulate pharmaceutical composition of the present invention is stored at accelerated conditions of 40° C./75% relative humidity, the rosuvastatin lactone impurity is less than 0.5% by weight of the composition. In preferred embodiments, the lactone impurity is less than 0.1% by weight of the composition. Further the multi-particulate pharmaceutical composition is said to be stable when the total impurities, which include anti-isomer (impurity A), 5-keto rosuvastatin, rosuvastatin lactone (impurity B), dehydro rosuvastatin acid, 5-keto rosuvastatin, dehydro lactone, dehydro triene and the highest unknown impurity, are less than 1.5%, preferably less than 1% by weight.

The term 'sprinkle' as used herein means that the multi-particulate pharmaceutical composition is to be added onto food or any edible material, or liquid, such as water, juices etc. before administration. The pellets of the multi-particulate pharmaceutical composition may be packed in sachet or pouch or filled into capsules and may be sprinkled onto food or edible material or into a liquid. Alternatively, multi-particulate pharmaceutical composition may also be in the form of a dispersible tablet which can be dispersed in a liquid to yield a dispersion of the individual particles before drinking. The multi-particulate pharmaceutical composition of the present invention is configured so as to be administered by initially opening a sachet or pouch or capsule filled with it or transferring it onto a vehicle, such as a soft food, for example applesauce, pudding, custard, oatmeal and yoghurt. Then, the vehicle into which the composition is sprinkled is swallowed immediately. It will be appreciated that the multi-particulate pharmaceutical composition of the present disclosure is not designed so as to be swallowed as a whole, and is meant to be sprinkled onto the vehicle. Alternatively, geriatric patients who have difficulty swallowing may adding the composition of the present invention that has been filled into sachet or pouch or capsule, into a liquid medium, such as water, to obtain a suspension. The suspension may be then orally administered through, e.g., a nasogastric tube into the stomach.

Rosuvastatin used in the multi-particulate pharmaceutical composition of the present disclosure, may be in different salt forms, such as alkali metal salts, such as lithium, sodium, potassium, and cesium and the like; and alkaline earth metal salts, such as beryllium, magnesium, and calcium salts and the like. The percentages of the rosuvastatin are expressed in terms of its acid and not salt. In one specific embodiment, calcium salt of rosuvastatin is used. It may be used as a crystalline or amorphous form. The particle size distribution of the rosuvastatin calcium may be such that $D_{10}$ ranges from about 2 microns to 20 microns, $D_{50}$ ranges from 30 microns to 70 about microns and $D_{90}$ ranges from about 120 microns to 200 microns, preferably, the $D_{10}$ is about 5 to 10 microns, $D_{50}$ is about 40 to 60 microns and $D_{90}$ is about 160 to 180 microns. In one most preferred embodiment, the particle size distribution of the rosuvastatin calcium is such that $D_{10}$ is about 6 microns, $D_{50}$ is about 50 microns and $D_{90}$ is about 160 microns. Generally, $D_{10}$ is not more than 20 microns, $D_{50}$ is about 25 microns to 50 microns and $D_{90}$ is not more than 200 microns. In one embodiment, the stable multi-particulate pharmaceutical composition of the present disclosure comprises, in one embodiment, at least 5% by weight of pharmaceutically acceptable salt of rosuvastatin as a sole active ingredient, by weight of the pellets. In one specific embodiment, the rosuvastatin is present in the form of its calcium salt. In a preferred embodiment, the amount of rosuvastatin or its salt ranges from about 5% by weight to about 30% by weight, preferably 5% by weight to 15% by weight of the pellets of the multi-particulate pharmaceutical composition. All the percentages of the rosuvastatin are expressed in terms of its free acid and not salt.

In one embodiment, for a strength of 5 mg of rosuvastatin, the total weight of the pellets is about 50 mg, for 10 mg of rosuvastatin, the total weight of the pellets is about 100 mg; for 20 mg of rosuvastatin; the total weight of the pellets is about 200 mg; for 40 mg of rosuvastatin, the total weight of the pellets is about 400 mg. It will be appreciated by person skilled in the art that the pellet volume is very compact and the patients can administer the prescribed dose of rosuvastatin with the help of very small portions of a vehicle, such as soft food, apple sauce and the like.

The multiparticulate composition of the present invention may contain osmotic release modifiers that accelerate the release of rosuvastatin from the pellets. Such osmotic release modifiers include agents that have good affinity for water, and which dissolve quickly when in contact with an aqueous medium. For the purpose of this disclosure, the osmotic release modifiers do not include large molecular weight carbohydrates such as, for instance, microcrystalline celluloses or sugars of sugar spheres. The osmotic release modifiers are rather ones that may be, e.g., low molecular weight carbohydrates that may be readily soluble in water such as mannitol, sucrose, lactose, fructose, lactitol or the salts of monovalent metal ions. The monovalent metal ion include, but are not limited to, sodium, potassium, lithium, cesium, or rubidium. The salts of monovalent metal ions as osmotic release modifiers are selected from the group consisting of, but are not limited to, sodium citrate, sodium phosphate, sodium bicarbonate, sodium chloride, potassium nitrate, potassium sulfate and mixtures thereof. They may be present in amounts of from about 1% by to 20% by weight, preferably 2% by weight to 10% and most preferably 3% by weight to 8% by weight of the stable multi-particulate pharmaceutical composition. The osmotic release modifier is used in amounts sufficient to cause the pellets to grow in size via the imbibition of water, and then swell, disintegrate or burst, thereby allowing for the release of the drug into the gastrointestinal tract. In preferred embodiments, it was found that the pellets burst is less than about 3 minutes, preferably, less than about 1 minute. This phenomenon enables the pellets to release the drug when a large quantity of aqueous medium, such as is present in the gastrointestinal tract, is available. It will be understood in the art that for this phenomenon to proceed unhindered, either the pellets should be uncoated or the coating if any, should be soluble or easily disintegrated in an aqueous medium. Particularly, the pellets should be free of a barrier coating such as a coating with a water insoluble polymer. The release does not occur when the pellets are sprinkled on soft food and ingested. In embodiments where pellets are harder because they are made by extrusion and spheronization, the preferred amount of osmotic release modifier is in the range of 3% to 8% by weight of the multi-particulate pharmaceutical composition. In one preferred embodiment of the present disclosure, the osmotic release modifier is sodium citrate in an amount from about 1% by to 20% by weight, preferably 2% by weight to 10% and most preferably 3% by weight to 8% by weight of the stable multi-particulate pharmaceutical composition.

The stable multi-particulate pharmaceutical composition comprises one or more stabilizers which are preferably alkaline earth metal salts. In one specific embodiment, the stabilizer is a salt of an alkaline earth metal. In such a specific embodiment, the stabilizer is not an inorganic substance, such as for example, titanium oxide or iron oxide, or any other tar-based pigment. When the stabilizer used is an alkaline earth metal, it is preferably selected from the group consisting of, but not limited to, magnesium hydroxide, magnesium oxide, magnesium acetate, calcium acetate, calcium gluconate, calcium glycerophosphate and aluminum hydroxide and mixtures thereof. The stabilizer is preferably present in the multi-particulate pharmaceutical composition in amounts of from about 1% to about 20% by weight, preferably 2% to 10% by weight and most preferably 3% to 8% by weight of the stable multi-particulate pharmaceutical composition. In one preferred embodiment of the present invention, the stabilizer is magnesium oxide which is present in an amount of from about 1% to 20% by weight, preferably 2% to 10% by weight and most preferably 3% to 8% by weight of the stable multi-particulate pharmaceutical composition.

Apart from osmotic release modifiers and stabilizers, the pellets may further comprise conventional excipients, such as disintegrants, diluents and lubricants. Examples of the disintegrants that may be used in the pellets include, but are not limited to, crospovidone, sodium starch glycolate, sodium croscarmellose, carboxymethylcellulose, low viscosity hydroxypropylcellulose, potassium polacrilin or mixtures thereof. The disintegrant may be present in an amount ranging from about 15% to about 50% by weight, preferably 20% to 35% by weight and most preferably 25% to 30% by weight of the stable multi-particulate pharmaceutical composition.

Examples of the diluents that may be used in the composition, include, but are not limited to, microcrystalline cellulose, lactose, starch, magnesium carbonate, maltose, kaolin or mixtures thereof. The diluents may be present in an amount ranging from about 15% to about 50% by weight, preferably 20% to 35% by weight and most preferably 25% to 30% by weight of the stable multi-particulate pharmaceutical composition.

In one embodiment, the pellets of the stable multi-particulate pharmaceutical composition may be prepared by extrusion and/or spheronization. In one specific embodiment, the stable multi-particulate pharmaceutical composition may be prepared by initially mixing rosuvastatin calcium, stabilizer, osmotic release modifier and other excipients and passing this powder blend through a suitable sieve. The blend is then granulated with a suitable granulating agent that may be, for example, purified water or any binder solution. The wet granules may be extruded and spheronized. The average particle size of the individual pellets of the pharmaceutical composition may be determined by sieve analysis using an ASTM sieve. The sieve analysis is a practice or procedure used to assess the particle size distribution of a granular material, wherein the sieve mesh size is represented by a micrometer average particle size through which the particles pass. The particle size can also be measured via a laser light diffraction technique. The laser light diffraction technique used for the determination of particle size and its distribution is based on the analysis of the diffraction pattern produced when particles are exposed to a beam of monochromatic light. In one embodiment of the present disclosure, the particle size distribution is determined by following the model of Malvern Mastersizer: Analysis model: Polydisperse, Presentation: BNJE, having a range lens: 300 mm, and Beam length of 2.40 mm. The term $D_N$ value of 'x μm' herein means at least about N % of the total population have a particle size less than 'x μm'.

When the particle size of the pellets is too large, it provides a gritty feeling when sprinkled on food that is not acceptable and desirable and may deter the user from administering the multi-particulate pharmaceutical composition as a sprinkle. The unique size range of the pellets of the composition of the present invention does not give a gritty feeling when sprinkled on food and administered or drank with a liquid vehicle.

In one specific embodiment, where the pellets are prepared by extrusion, spheronization, the extrudates so formed may be sieved to achieve the average diameter of the pellets, preferably wherein 95% of the pellets pass through size 20 mesh and 100% of the pellets are retained on size 40 mesh. Typically, in one specific embodiment, the pellets have an average diameter of from about 0.1 mm to 0.9 mm, preferably from about 0.2 mm to 0.8 mm and most preferably the pellets have an average diameter of about 0.4-0.7 microns.

The rosuvastatin calcium containing pellets may be optionally, coated with a taste masking coating composition. Examples of polymers that may be used as a taste masking coating include, dimethylaminoethyl methacrylate (Eudragit EPO), polyvinyl alcohol, low viscosity cellulose derivatives and the like and mixtures thereof. The coated pellets are then lubricated and may be filled into a capsule or a sachet or a pouch or may be compressed into a dispersible tablet. In one specific embodiment, the present invention provides pellets comprising an admixture of rosuvastatin calcium, magnesium oxide and sodium citrate and other excipients. The pellets are further coated with a taste masking coating comprising low molecular weight hydroxypropyl methyl cellulose and low molecular weight polyethylene glycol. In one specific embodiment, the present invention provides a stable multi-particulate pharmaceutical composition comprising pellets, the pellets comprising a mixture of rosuvastatin or its pharmaceutically acceptable salts as a sole active ingredient, one or more osmotic release modifiers and one or more stabilizers, wherein the particle size of the pellets ranges from about 0.4 mm to 0.8 mm, the rosuvastatin salt is rosuvastatin calcium, the stabilizer is an alkaline earth metal salt and the osmotic release modifier is inorganic salt of monovalent cation.

In one aspect, the present invention also provides a method of treating hypercholesterolemia, particularly in subjects having difficulty swallowing. In one particular aspect, there is provided a method of treatment of hyperlipidemia, mixed dyslipidemia, hypertriglyceridemia, homozygous familial hypercholesterolemia, or primary dysbetalipoproteinemia, slowing the progression of atherosclerosis, primary prevention of cardiovascular disease, said method comprising orally administering to a human in need thereof the stable multi-particulate pharmaceutical composition of the present invention. The method of treating includes administration of the pharmaceutical composition of the present invention comprising administration of from about 5 to about 40 mg of rosuvastatin composition per day, the quantity being expressed as the free acid.

In one embodiment, the stable multi-particulate pharmaceutical composition filled into a capsule is opened by a capsule opening device to avoid spillage of the contents of the capsule while opening the capsule. This is particularly helpful for geriatric patients who have difficulty opening the capsules to empty the contents onto soft food. Particularly, the absence of fines in the multi-particulate pharmaceutical composition avoids the loss of the composition which may result from blowing of the fine powder while being emptied from the capsule or pouch onto the carrier solid or liquid food contents. Alternatively, the pellets can be administered from a device which dispenses the pellets directly onto the soft food.

The following examples illustrate the scope of the present disclosure without any limitation thereto.

COMPARATIVE EXAMPLE 1

Rosuvastatin calcium, microcrystalline cellulose, mannitol and crospovidone were mixed in a polybag and sifted through suitable sieve. Additional mannitol was dissolved in purified water and used as a granulating solution. The rosuvastatin calcium mixture was granulated with the mannitol/purified water solution. The resulting wet granules were passed through an extruder. The extrudates were then passed through a spheronizer to form pellets. The wet pellets were dried and the dried pellets were suitably sized. A solution of cellulose acetate and polyethylene glycol was prepared in an acetone and water mixture. The dried pellets were coated with the above solution. The coated pellets were dried and lubricated with silicon dioxide. The lubricated pellets were then filled into hard gelatin capsules.

TABLE 1

| In-vitro dissolution data of Comparative Example 1 in different dissolution media | | |
|---|---|---|
| Time (min) | 0.01N HCl, pH 1.2 | Acetate buffer, pH 4.5 |
| 10 | 29 | 41 |
| 20 | 46 | 60 |
| 30 | 58 | 71 |
| 45 | 70 | 82 |

From Table 1, it is evident that the Comparative Example 1 provided poor dissolution in 0.01 N HCl as well as acetate buffer. For instance, in 0.01 N HCl and in an acetate buffer, not more than about 80% was released, at the end of 30 minutes.

The filled capsules of Comparative Example 1 were subjected to accelerated stability studies wherein the filled capsules were stored at 40° C. and 75% relative humidity for two months and the results are provided in Table 2.

TABLE 2

Results of stability study of Comparative Example 1

| | Anti-isomer (IMP A) | 5-keto | Lactone (IMP B) | Dehydro Acid | 3-keto | Dehydro lactone | Dehydro triene | Highest Unknown impurity | Total impurities |
|---|---|---|---|---|---|---|---|---|---|
| Initial | ND | 0.35 | 0.03 | 0.01 | ND | ND | ND | 0.05 | 0.47 |
| 2 months 40° C./75% RH | 0.01 | 0.49 | 0.46 | 0.01 | ND | 0.01 | ND | 0.06 | 1.3 |

ND: not detectable

From the data given in Table 2, it is evident that the multi-particulate pharmaceutical composition showed very high total impurity. For example, the total impurities increased from 0.47% to 1.3% at the end of just two months under accelerated temperature and humidity conditions. Further the in vitro dissolution was not satisfactory in that roughly 60%-70% of the rosuvastatin calcium was released at the end of 30 minutes.

COMPARATIVE EXAMPLE 2

Trisodium citrate dihydrate was dissolved in water. Rosuvastatin calcium, microcrystalline cellulose, mannitol and crospovidone were mixed and sifted through a suitable sieve. This blend was granulated with the trisodium citrate solution. The wet granules were extruded through an extruder. The extrudates were then passed through a spheronizer to form pellets. The pellets were dried in a fluid bed drier and were suitably sized by passing through ASTM #20 sieve and collecting the them on ASTM #40 sieve to have mean size ranging 0.4 mm to 0.8 mm. A solution of low viscosity hydroxypropyl methyl cellulose and polyethylene glycol was prepared in isopropyl alcohol and water. The dried pellets were coated with this solution. The coated pellets were then lubricated with silicon dioxide and filled into hard gelatin capsule shells.

TABLE 3

In-vitro dissolution data of Comparative Example 2 in various dissolution media

| Time (min) | 0.01N HCl, pH 1.2 | Acetate buffer, pH 4.5 |
|---|---|---|
| 10 | 66 | 75 |
| 20 | 81 | 91 |
| 30 | 89 | 96 |
| 45 | 93 | 98 |

The filled capsules of Comparative Example 2 were subjected to accelerated and long term stability conditions for three months at 40° C. and 75% relative humidity and the results are provided in Table 3 and 4, respectively.

TABLE 4

Results of the stability study of Comparative Example 2

| | Anti-isomer | 5-keto | Lactone (IMP B) | Dehydro Acid | 3-keto | Dehydro lactone | Dehydro triene | Highest unknown impurity | Total impurities |
|---|---|---|---|---|---|---|---|---|---|
| Initial | 0.01 | 0.39 | 0.07 | 0.01 | ND | ND | ND | 0.05 | 0.60 |
| 3 months 40° C./75% RH | ND | 0.11 | 1.06 | ND | ND | 0.06 | ND | 0.33 | 2.66 |

ND: not detectable

From the results of the dissolution tabulated in Table 3 above, it is apparent that capsules of Comparative Example 2 provided satisfactory dissolution. For instance, complete dissolution of rosuvastatin calcium was observed in 0.01 N HCl and acetate buffer. However, from the results of the stability studies, given in Table 4, it can be concluded that there is sharp increase in the rosuvastatin lactone impurity content, highest unknown impurity and the total impurities, upon exposure to time and temperature and relative humidity. For instance, at the end of three months, at 40° C./75% relative humidity, the total impurities increased from an initial value of 0.60% by weight to 2.66% by weight.

EXAMPLE 1

Trisodium citrate dihydrate was dissolved in water. Rosuvastatin calcium, microcrystalline cellulose, mannitol, crospovidone and magnesium oxide were mixed well and sifted through a suitable sieve and granulated with the trisodium citrate solution. The wet granules were extruded through an extruder and spheronized in a spheronizer. The resulting pellets were then dried and passed through ASTM #20 sieve and collected on ASTM #40 sieve to have mean particle size ranging from 0.4 mm to 0.8 mm.

A solution of low viscosity hydroxypropyl methyl cellulose and polyethylene glycol was prepared in an isopropyl alcohol and water mixture. The rosuvastatin calcium pellets were coated with the solution and dried. The coated pellets were mixed with silicon dioxide. The resulting lubricated pellets were filled into hard gelatin capsule shells.

TABLE 5

In-vitro dissolution data of Example 1 in various dissolution media

| Time (min) | 0.01N HCl, pH 1.2 | Acetate buffer, pH 4.5 |
|---|---|---|
| 5 | 70 | 67 |
| 10 | 90 | 91 |
| 20 | 96 | 98 |
| 30 | 96 | 99 |
| 45 | 97 | 100 |

The above capsules filled with pellets were subjected to accelerated, intermediate and long term stability conditions, and the chemical analysis in terms of assay, and known and unknown impurities was performed, as shown in Table 6.

TABLE 6

Results of the stability study of the pharmaceutical composition of Example 1

| | Anti-isomer | 5-keto | Lactone | Dehydro Acid | 3-keto | Dehydro lactone | Dehydro triene | Highest unknown impurity | Total impurities |
|---|---|---|---|---|---|---|---|---|---|
| Initial | ND | 0.39 | ND | 0.01 | ND | 0.01 | ND | 0.05 | 0.61 |
| 6 months 40° C./75% RH | ND | 0.06 | 0.02 | 0.01 | ND | ND | ND | 0.18 | 0.67 |

ND: not detectable

It can be observed from Table 5 that the multi-particulate pharmaceutical composition of the present invention showed complete dissolution in various dissolution media. Further, it is evident from the above Table 6, that rosuvastatin lactone impurity levels remained substantially unchanged as compared to the initial concentration. This is remarkable when compared to the results of Comparative Examples 1 and 2.

The invention claimed is:

1. A stable multi-particulate pharmaceutical composition comprising pellets prepared by extrusion and spheronization of a mixture consisting of
   (i) rosuvastatin or its pharmaceutically acceptable salts as a sole active ingredient present in an amount ranging from about 5% by weight to about 30% by weight of the multi-particulate pharmaceutical composition,
   (ii) one or more osmotic release modifiers in an amount sufficient to cause the pellets to grow in size via an imbibition of water ranging from 1% to 20% by weight, and then, disintegrate or burst, selected from a group consisting of mannitol sucrose, lactose, fructose, lactitol sodium citrate, sodium phosphate sodium bicarbonate, sodium chloride, potassium sulfate and mixtures thereof
   (iii) one or more stabilizers selected from a group consisting of magnesium hydroxide, magnesium oxide, magnesium acetate, calcium acetate, calcium gluconate, calcium glycerophosphate and aluminum hydroxide and mixtures thereof present in an amount ranging from about 1% to about 20% by weight,
   (iv) a diluent, selected from a group consisting of microcrystalline cellulose, lactose, starch, magnesium carbonate, maltose, low viscosity hydroxypropylcellulose kaolin or mixtures thereof, present in an amount ranging from about 15% to about 50% by weight and
   (v) a disintegrant selected from a group consisting of crospovidone sodium starch glycolate, sodium croscarmellose, carboxymethylcellulose, low viscosity hydroxypropylcellulose, potassium polacrilin or mixtures thereof; present in an amount ranging from about 15% to about 50% by weight wherein:
(a) the pellets are surrounded by a taste masking coating but are free of a barrier coating of a water insoluble polymer;
(b) the pellets have an aspect ratio of 1 to 2;
(c) the pellets are filled in a capsule, sachet, or pouch;
(d) the pellets when sprinkled on soft food do not release the rosuvastatin or its pharmaceutically acceptable salts;
(e) the stable multi-particulate pharmaceutical composition is free from pellets that have a size greater than 0.8 mm, which would be prevented from passing through an ASTM #20 sieve, and is also free from pellets that have a size less than 0.4 mm, which would pass through an ASTM #40 sieve; and
(f) the composition, when tested for dissolution in 0.01 N HCl at a pH of 1.2 or in an acetate buffer at a pH 4.5, releases at least 80% of the rosuvastatin or its pharmaceutically acceptable salts within 10 minutes.

2. The stable multi-particulate pharmaceutical composition of claim 1, wherein the rosuvastatin is present in the form of its calcium salt.

3. The stable multi-particulate pharmaceutical composition of claim 1, wherein the osmotic release modifier is a salt of a monovalent metal ion.

4. The stable multi-particulate pharmaceutical composition of claim 3, wherein the osmotic release modifier is sodium citrate.

5. The stable multi-particulate pharmaceutical composition of claim 1, wherein the stabilizer is magnesium oxide.

* * * * *